United States Patent [19]

Koehler et al.

[11] Patent Number: 5,693,228

[45] Date of Patent: Dec. 2, 1997

[54] METHOD AND DEVICE FOR VIBRATION DURING SOLID PHASE MICROEXTRACTION

[75] Inventors: Wulf Hinrich Koehler, Messel; Helmut Gunther-Heinz Geppert, Cottbus, both of Germany

[73] Assignee: Varian Associates, Inc., Palo Alto, Calif.

[21] Appl. No.: 534,936

[22] Filed: Sep. 28, 1995

[51] Int. Cl.$^6$ .................................................. B01D 15/08
[52] U.S. Cl. .................... 210/656; 210/198.2; 210/511; 422/50; 422/59; 436/163
[58] Field of Search ............................ 210/634, 656, 210/198.2, 511; 422/58, 59, 102; 436/163, 169

[56] References Cited

U.S. PATENT DOCUMENTS

| | | | |
|---|---|---|---|
| 4,521,622 | 6/1985 | Andoh et al. | 564/406 |
| 4,930,898 | 6/1990 | Miller-Ihli | 422/50 |
| 5,403,489 | 4/1995 | Hagen et al. | 210/638 |
| 5,496,741 | 3/1996 | Pawliszyn | 436/163 |
| 5,565,622 | 10/1996 | Murphy | 73/61 |

*Primary Examiner*—Ana Fortuna
*Attorney, Agent, or Firm*—Edward H. Berkowitz

[57] ABSTRACT

An apparatus is described for carrying out solid phase microextraction and analysis of analytes in a fluid carrier in which a fiber within a housing is vibrated by a vibrating means during microextraction. The housing contains access means so that the carrier and analytes can be brought into contact with the vibrating fiber during the extraction stage. In a preferred embodiment of the present invention, the vibrating means comprises a membrane, a solenoid for vibrating the membrane, a frame, a retainer mounted on the frame for holding the solenoid, a holder for the membrane, and a retainer arm having one end connected to the retainer and the other end attached to the holder. A method for microextraction and analysis is also described in which a vibrating fiber is placed into contact with analytes to be analyzed in a suitable carrier deposited in a container for a sufficient period of time for microextraction to occur. Subsequently the fiber is removed and placed into a suitable analytical instrument for desorption and analysis with respect to at least one component on the fiber.

24 Claims, 4 Drawing Sheets

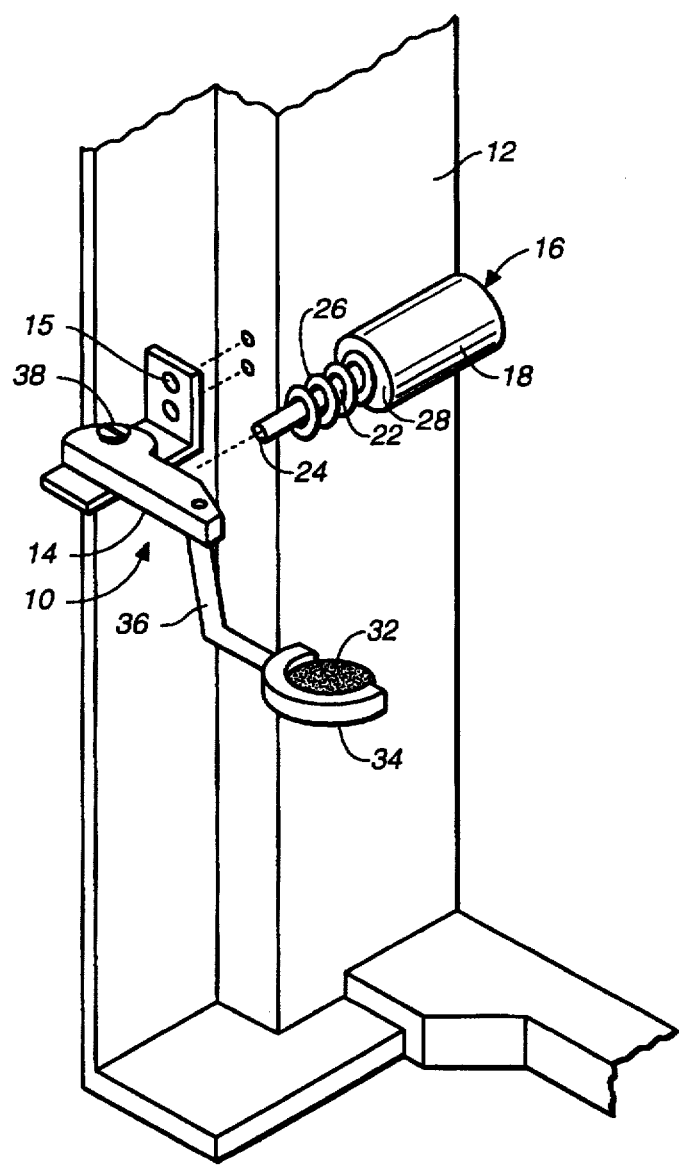
FIG._1
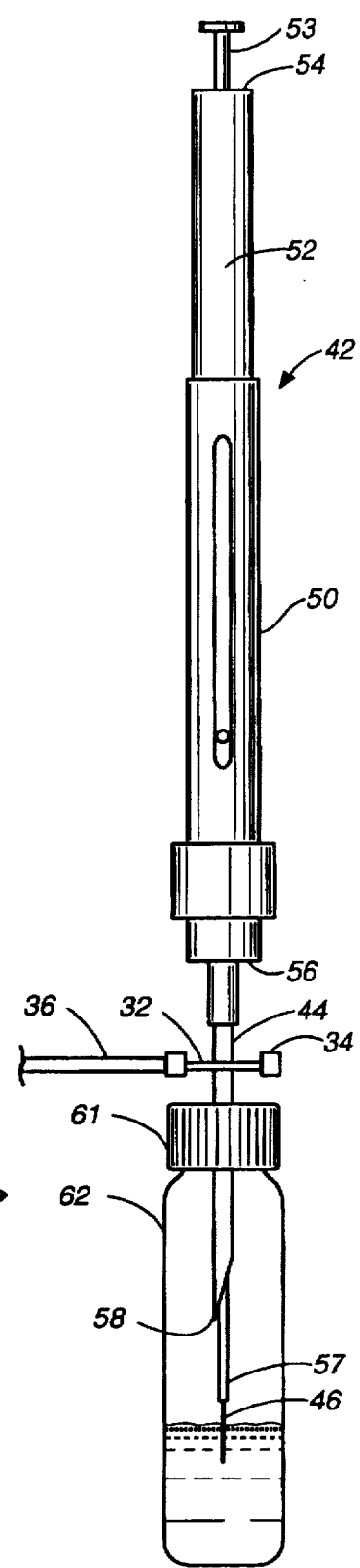
FIG._2A

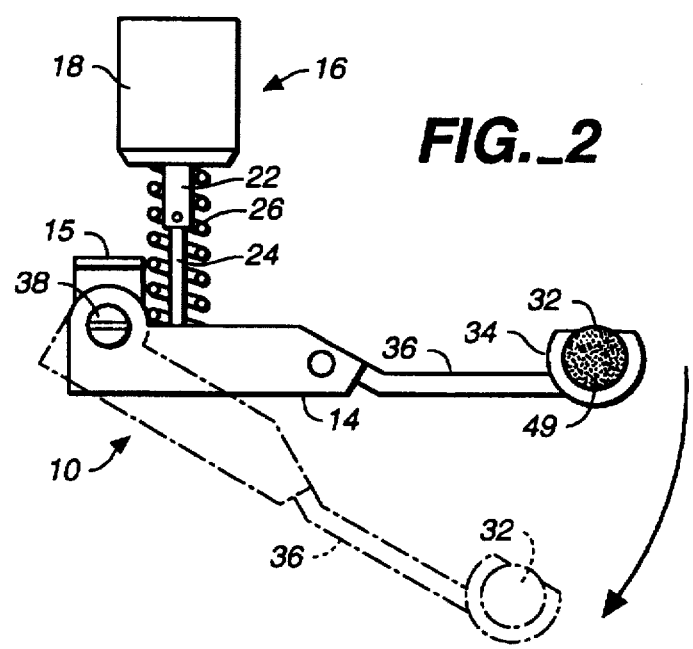
FIG._2
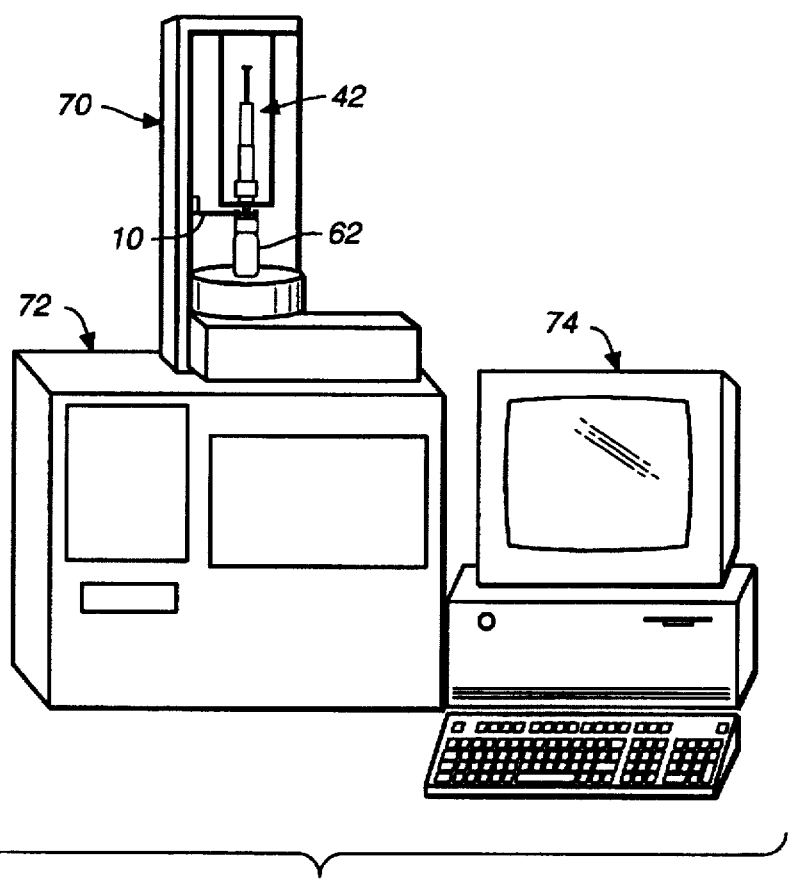
FIG._4

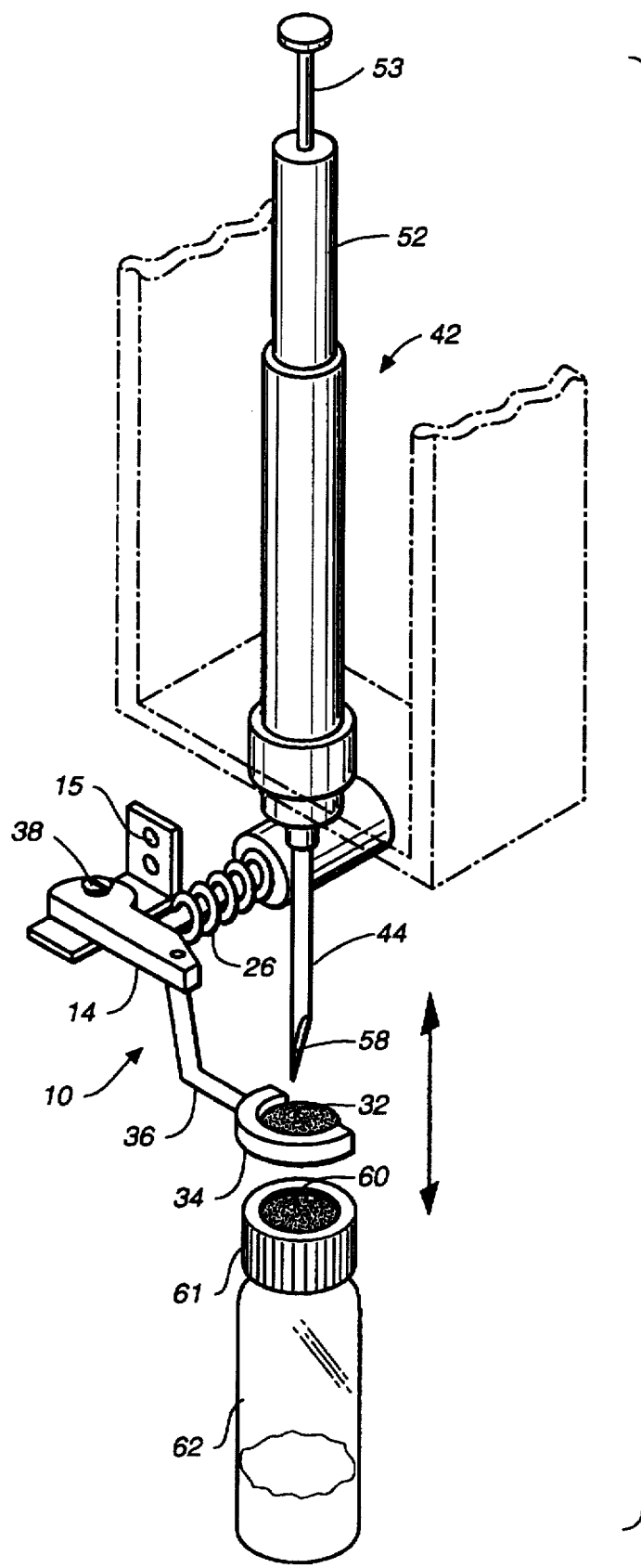
FIG._3

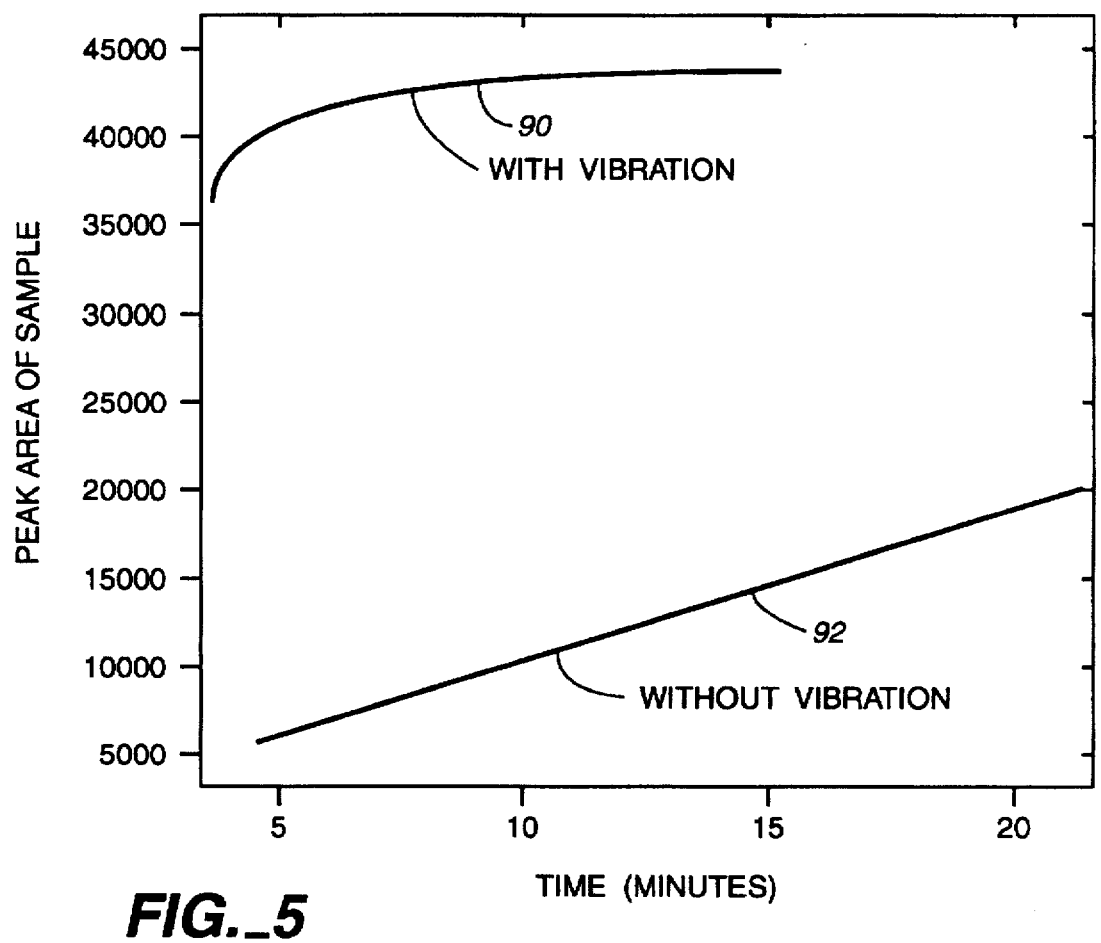
FIG._5

METHOD AND DEVICE FOR VIBRATION DURING SOLID PHASE MICROEXTRACTION

BACKGROUND OF THE INVENTION

1. Field of the Invention

This invention relates to a method and device for vibration during solid phase microextraction and analysis. In particular, this invention relates to microextraction being carried out with vibration of various types of a single fiber or multiple fibers to increase the rate of adsorption of the fiber of analytes in the sample being analyzed.

2. Description of the Prior Art

The organic analyses of environmental samples involve the separation of analytes (components) of interest from such matrices as soil, water, fly ash, tissue or other material. Liquid extraction is traditionally used as the separation process. For example, water samples are usually extracted with organic solvent. Similarly, solid samples are leached with an organic solvent in a SOXHLET apparatus. Methods based on solvent extraction are often time consuming, difficult to automate and are very expensive since they require high purity organic solvents and these organic solvents involve significant purchase and disposal costs. Further, the organic samples may have high toxicity and often are difficult to work with. In addition, the extraction processes can be highly non-selective. Therefore, sequential chromatographic techniques must sometimes be used to separate complex mixtures after extraction, significantly increasing the overall analysis time and the cost.

Solid phase extraction is a known effective alternative liquid-to-liquid extraction in the analysis of aqueous samples. The primary advantage of solid phase extraction is the reduced consumption of high purity solvents and the resulting reduction in laboratory costs and solvent disposal costs. Solid phase extraction also reduces the time required to isolate the analyte of interest. However, solid phase extraction continues to use solvents and often suffers from high blank values. Further, there is considerable variation between the products offered by different manufacturers and lot-to-lot variation can be a problem when carrying out solid phase extraction procedures. Solid-phase extraction cartridges available from manufacturers are typically constructed of plastic, which can adsorb the analyte and increase interferences in the analysis. The disposable plastic cartridges used in the solid phase extraction process are first activated using organic solvent. The excess organic solvent is then removed and the sample to be tested is passed through the cartridge. The organic analytes from the sample are adsorbed on the chemically modified silica surface of the material in the cartridge. Both molecules of interest as well as interferences are retained on the cartridge material. During desorption, a selective solvent is chosen to first remove the interferences. The analyte is then washed out of the cartridge. The analytical procedure from that point on is identical to that used in liquid-liquid extraction. The analyte is first preconcentrated by evaporating down the extract and the mixture is then injected into an appropriate high resolution chromatographic instrument. Steps involving the use of organic solvents are the most time consuming.

Solid phase microextraction, or SPME, was developed as the alternative to the foregoing prior art methods of preparing samples in a fluid carrier for chromatographic analysis; see Pawliszyn, Janusz, WO 91/15745, International Publication Date of Oct. 17, 1991. SPME involves using a fiber that is mounted within a hollow needle of a syringe (e.g., a modified gas chromatography (GC) syringe). The fiber, for example is a fused silica fiber coated with an adsorbent that acts as a "sponge" to extract a sample and to concentrate the organic analytes on its surface so that it can be transferred into the heated injector of the GC. While in the injector, the analytes are thermally desorbed from the fiber and transferred into the GC column for analysis. With SPME, one can achieve detection limits down to the parts-per-trillion (ppt) range for a wide number of volatile and semi-volatile compounds. Pertinent portions of the Pawliszyn reference that define details of the SPME unit are incorporated by reference herein.

The chief disadvantage of the use of SPME is the time required to extract the sample by the coated fibers. For example, when a water matrix sample containing one or more analytes of interest is desired to be analyzed and is contained in a typical sample vial containing a septum, the needle of the syringe of the SPME device is inserted through the septum. The plunger of the syringe is depressed and the exposed coated fiber extends from the free end of the needle and is inserted either above (headspace sample) or into the water matrix sample (liquid sample). In this manner, the fiber will not be damaged by the septum of the sample vial. For example, organic analytes that may be found in water can be extracted into a non-polar phase coated onto the fiber. Water is considered to be the carrier in a water matrix sample. When the microextraction has occurred to a sufficient degree, the plunger is moved to the withdrawn position causing the fiber to be drawn into the needle and the needle is removed from the sample bottle through the septum. The time for fiber adsorption of the analytes to be extracted will depend on many factors including the analytes themselves as well as the thickness and type of coating, if any, on the fiber. Typically the equilibrium adsorption time ranges from 1 to 30 minutes, with some analytes requiring up to several hours. In the preferred method of operating SPME, the sample is stirred or the vial is rotated to impart forceful agitation of the sample during the time the fiber is present in the vial during the extraction stage of the analysis in order to decrease the adsorption time. The stirring can be done by placing a magnetic bar within the analyte and by using a conventional magnetic stirrer. Another method for agitation is to induce ultrasonic vibrations within the liquid sample in the vial. It has been found that the adsorption time can be reduced from about 30 minutes range to approximately two minutes with forceful agitation; see FIG. 9 at page 1194 of D. Louch, S. Motlagh, and J. Pawliszyn, *"Dynamics of Organic Compound Extraction From Water Using Liquid-Coated Fused Silica Fibers"*, Analytical Chemistry, Vol. 84, No. 10, pages 1187–1199 (May 15, 1992).

It has been found that to provide sufficient sample agitation to significantly reduce the adsorption time using the above method, mechanical and electrical part damage can occur. Under some cases of forceful agitation, the vials have been known to crack and even to break. In addition, the use of magnetic and other conventional stirring means added to the sample introduces a potential source of contamination. A disadvantage of using ultrasound agitation of the sample is the unwanted rise in the temperature of the sample which adds an unwanted and uncontrollable variable to the analysis since adsorption efficiency is temperature dependant.

After the extraction stage, the plunger is moved to a withdrawn position to retract the fiber within the needle and the needle is removed from the bottle. During the analysis stage, the needle is inserted through the septum of an injection port of a conventional gas chromatograph or other suitable analytical instrument.

There is a need for an alternative method to reduce the equilibrium adsorption time during the SPME extraction stage without the inherent disadvantages found with the prior art methods of agitation.

SUMMARY OF THE INVENTION

An improvement in a device for carrying out solid phase microextraction of analytes contained in a fluid carrier comprises a fiber, a housing surrounding the fiber and a vibrating means for vibrating the fibers. The housing contains access means so that the carrier and analytes are brought into contact with the vibrating fiber during the extraction stage.

The improvement in the prior art method of carrying out SPME with analytes contained in a carrier is the use of a vibrating fiber during the period of time the fiber is in the sample vial during the extraction step of SPME. The SPME and analysis method is characterized by contacting the vibrating fiber for a sufficient time to allow microextraction to occur, ending the contact and placing the fiber in a suitable analytical instrument in such a manner that desorption occurs with respect to at least one component on the fiber.

In one embodiment of the present invention, the vibrating means or vibrator comprises a membrane, a solenoid for vibrating the membrane, a frame, a retainer mounted on the frame for holding the solenoid, a holder for the membrane, and a retainer arm having one end connected to the retainer and the other end attached to the holder. The membrane comprises an elastomeric material capable of being pierced by a syringe needle that houses a fiber of an SPME unit. Suitable examples of the membrane are rubber, butadiene rubber, silicone rubber and similar materials. During the extraction stage, the end of the fiber that extends from the tip of the needle and into the sample vial is caused to vibrate by the vibration induced by the vibrating membrane.

BRIEF DESCRIPTION OF THE DRAWINGS

FIG. 1 is perspective view of the vibrator of the present invention;

FIG. 2 is a schematic top view of the vibrator of the present invention;

FIG. 2A is a side view of the syringe of an SPME unit of the present invention shown within a sample vial during the microextraction state;

FIG. 3 is a perspective view of the vibrator of the present invention in combination with the syringe within a housing of an SPME unit;

FIG. 4 is a perspective view of the vibrator of the present invention in combination with an SPME autosampler unit, a GC unit or other suitable analytical instrument and a personal computer programmed to operate the combination; and FIG. 5 is a graph of an amount of analyte extracted versus time with and without the vibrator.

DESCRIPTION OF A PREFERRED EMBODIMENT

Referring to FIGS. 1 and 2, vibrator 10 is shown mounted to frame 12 by means of bracket 15 of a typical SPME unit by means of retainer 14 which is fixedly attached to frame 12. More particularly, spring-biased solenoid 16 comprises coil (not shown) within cylinder 18, lead 22 fixedly attached to rod 24 connecting solenoid 16 to retainer 14 and spring 26 positioned between retainer 14 and end 28 of cylinder 18. Membrane 32 is within holder 34 and is joined to retainer 14 by arm 36. Solenoid 16 is designed to move retainer 14 and arm 36 about pivot post 38 when vibrator 10 is in the static OFF position.

FIG. 2A shows syringe 42 of a typical SPME unit (depicted in FIG. 4) combined with vibrator 10 having needle 44 containing a fiber 46 which is caused to vibrate when vibrator 10 cycles between a static ON position and a static OFF position. During the static ON position of vibrator 10 shown in FIG. 2A, spring 26 is compressed by action of solenoid 16 which returns arm 36 and retainer 14 containing membrane 32 into alignment directly under needle 44 of syringe 42 which is poised to pierce center 49 of membrane 32. Syringe 42 is made up of barrel 50 which contains plunger 52 and is slidable within the barrel 50. Plunger 52 has a handle 53 extending from one end 54 of barrel 50. Needle 44 is located at the other end 56 of barrel 50.

Fiber 46 is a solid thread-like material that is extendable from the needle 44 through the barrel 50 and out end 56. The end (not shown) of fiber 46 located adjacent to handle 53 has retention means (not shown) located thereon so that the fiber will move longitudinally as plunger 52 slides within barrel 50. The retention means can be simply a drop of epoxy which is placed on the end of the fiber 46 near the handle 53 and allowed to harden. Fiber 46 is partially enclosed within metal casing 57 which surrounds that portion of the fiber 46 located within the plunger 52, barrel 50 and part of the needle 44. The purpose of the metal casing is to protect the fiber 46 from damage and to ensure a good seal during operation of the device.

In general terms, syringe 44 is a typical housing for the fiber 46 and the access means is the action of plunger 52 in moving fiber 46 beyond tip 58 of needle 44. The diameter of the fibers will vary, but will preferably be between 0.05 millimeters and 1 millimeter. Fused silica fibers, which are widely used in optical communication and are often referred to as optical fibers, can be used as the composition for fiber 46. Fiber 46 can be modified by preparing its surface by etching procedures to increase the surface area followed by chemical attachment with a desired coating. The fiber coatings can consist of solid polymeric materials such as polydimethylsiloxane (PDMS) and polyacrylate or graphite. The fibers themselves can be based as a substrate of fused silica, wires of various metals, and similar materials. Other fiber coatings can be carbowax, silicone, polyimide, octadecyltrichlorosilane, polymethylvinylchlorosilane, liquid crystalline polyacrylates, grafted self-assembled monolayers and inorganic coatings and combination of the aforementioned coatings. It is the vibrating of the fiber that is contacted by the carrier and analytes in the device of the present invention. One specific example of such coated fibers consists of fused silica fibers commercially available from Polymicro Technologies Inc., Phoenix, Ariz., coated with a polyamide film, and having an outer diameter of approximately 171 ppm. The normal lifetime for a prepared fiber is about 10 to several hundred injections with regular use.

In FIGS. 2 and 2A, membrane 32 of vibrator 10 is shown during the extraction stage. In this stage, needle 44 has pierced center 49 of membrane 32 and the center of septum 60 (shown in FIG. 3) within cap 61 on sample vial 62. The distance between membrane 32 and septum 60 is about $\frac{1}{16}$ to about $\frac{3}{4}$ inch and preferably about $\frac{1}{4}$ to about $\frac{1}{2}$ inch. Plunger 54 is fully extended to lower fiber 46 below tip 58 of needle 44 and vibrator 10 is oscillated in its static ON and OFF positions causing fiber 46 to vibrate.

Spring biased solenoid 16 is driven by an oscillatory drive signal (referred to herein as an oscillator), which may be generated by a number of electrical circuits well known to the art. As an example, solenoid 16 may be driven by a standard solenoid driver or switch driver, such as the switch mode solenoid driver L294 which is manufactured by National Semiconductor Corporation. Such drivers generally comprise a matrix of switches which couple and de-couple each of the terminals of solenoid 16 to respective voltage supply rails in synchronization with the state of a digital input signal provided to the driver. The input signal comprises a series of pulses, either repetitive or periodic in nature, which may be generated by a number of pulse generators and pulse-width modulators well known to the art. If the driver does not provide commutation paths, a commutation rectifier may be coupled between each solenoid terminal and the opposite voltage rail to provide a conduction path for the solenoid's current when the driver shuts power off to solenoid 16. The opposite voltage rail is the rail which is respectively coupled to the other solenoid 16 terminal. Such commutation rectifiers are well known to the art, and are also referred to as "flyback" or "freewheeling" rectifiers. The implementations of the driver and pulse generating circuits for solenoid 16 are not essential features of the present invention and are not essential to practicing the present invention. A detailed description of these circuits is not required for one of ordinary skill in the art to make and use vibrator 10 of the present invention.

As an additional embodiment of the present invention, spring biased solenoid 16 may be replaced by a two-coil solenoid, with each coil alternately attracting the solenoid's actuator to cause fiber 46 to vibrate. As yet another embodiment, solenoid 16 may be mounted only on the arm, without a mechanical connection to frame 12 as shown in FIG. 1. The motion of the solenoid's actuator causes vibrations in the fiber due to the switching of the actuator's momentum. In this embodiment, a spring-biased solenoid or a two-coil solenoid may be used. As yet another embodiment, a small motor having an un-balanced load (e.g., an eccentric flywheel) coupled to its shaft may be attached to arm 36. The rotation of the un-balanced load by the motor generates vibrations which are coupled to fiber 46 through membrane 32 and arm 36. As yet another embodiment, membrane 32 may be vibrated by a connecting rod which is moved by an electric motor mounted on the frame, with the connecting rod being coupled to the motor shaft by an eccentric cam.

In the preferred embodiment shown in FIGS. 1–4, spring-biased solenoid 16 is oscillated between the static ON and static OFF positions at a frequency of about 5 to about 40 cycles per second, preferably about 10 to about 30 cycles per second. FIG. 3 shows the end of the microextraction state when vibrator 10 momentarily returns to the static ON position, the vibrations cease, and needle 44 returns to its place above sample vial 62. Spring 26 of solenoid 16 remains in compression. Thereafter, vibrator 10 is in the static OFF position in which spring 26 is released and arm 36 and retainer 14 are pivoted laterally about pivot post 38 (e.g., approximately 30° in a clockwise direction as shown in FIG. 2). Therefore, during the static OFF position, arm 36 attached to holder 34 containing membrane 32 is moved so that membrane 32 is no longer directly over septum 60. The vibrator 10 cycle returns to the static ON position so that spring 26 is again compressed and arm 36 and retainer 14 are moved into position with membrane 32 directly over septum 60 within cap 61 of sample vial 62 and needle 44 enters vial 62 before the next stage of the vibrator 10 cycle. In that stage, the oscillations between the static ON and static OFF positions causes spring 26 to attempt to compress and release at the same frequency as the oscillator. This causes arm 36, retainer 14 and membrane 32 to move to and fro at this frequency. Because needle 44 is trapped within membrane 32 and septum 60, needle 44 is rapidly vibrated, which in turn causes fiber 46 within sample vial 62 to also vibrate at the same frequency as the oscillator. As a result of the apparatus of the present invention, there is at least an exponential increase in the rate of adsorption of the component(s) over an SPME unit without such a vibrator.

The term "vibration" as used to define the apparatus and method of the present invention is intended to mean physically induced oscillation, i.e., a back and forth motion from a physical force in comparison to motion from an indirect source such as vibration from an ultrasonic source or vibration from stirring the sample media. More particularly, the phrase "vibrating fiber(s)" as used to define the apparatus and method of the present invention is intended to mean fibers that are being oscillated at a frequency in the range of about 5 to about 40 vibrations per second and preferably in the range of about 10 to about 30 cycles per second.

The SPME method and analysis consists of a few simple steps. For example, when a water matrix sample containing analytes of interest is desired to be analyzed, the plunger of the syringe is depressed and the exposed fiber extending from the free end of the needle is inserted into the water matrix sample. The organic analytes of the water are extracted into the non-polar phase. Water is considered to be the carrier in a water matrix sample. Where the water sample is contained in a bottle containing a septum, the needle is inserted through the membrane of the vibrator and the septum before the plunger is depressed so that the fiber will not be damaged by either the vibrator membrane or the septum. When the microextraction has occurred to a sufficient degree into vibrating fiber 46, vibrator 10 is moved to the static ON position with spring 26 still in its compressed state. In that position, plunger 54 is moved to the withdrawn position causing fiber 46 within casing 57 to be drawn into needle 44 and needle 44 is removed from sample bottle 62 through septum 60 and then through vibrator membrane 32. The exact time for extraction will depend on many factors including the analytes (components) being extracted as well as the thickness and type of coating, if any, on the fiber. Usually, the extraction time is approximately two minutes. The needle is then inserted through the septum in an injection port of a conventional GC or other suitable analytical instrument. The plunger is then depressed again to expose the fiber and the organic analytes on the fiber are thermally desorbed and analyzed. The fiber remains in the analytical instrument during the analysis. When the analysis has been completed, the plunger is moved to the withdrawn position and the syringe is removed from the injection port.

While various types of syringes will be suitable, a HAMILTON 7000 (a trade mark) series syringe has been found to be suitable. The syringe facilitates convenient operation of the SPME process and protects the fiber from damage during the introduction through the membrane and septum into a sample bottle or into an injector of an analytical instrument or even during storage. The length of the fiber depends on the injector of the analytical instrument with which the fiber will be used.

The device and method of the present invention preferably utilizes a mechanical device such as SPME autosampler 70 in combination with analytical instrument 72 depicted in FIG. 4. Autosampler 70 can be programmed and operated by personal computer 74 to operate plunger 52 at the appropriate time to cause SPME syringe 44 to pierce membrane 32 of vibrator 10 and septum 60 during the extraction state, to control the three states of solenoid 16, and to insert needle 44 and fiber 46 into the injection port (not shown) of the analytical instrument 72. Autosampler 70 has an advantage over manual extraction and analysis in that the contact time and the length of the fiber in the carrier as well as in the instrument can be maintained constant. Either VARIAN 3400CX gas chromatograph or VARIAN 8200 CX AutoSampler has been found to be suitable. Vibrator 10 is mounted on frame 76 of autosampler 70 adjacent to sample vials 62.

A comparison between SPME with (90) and without (92) use of vibration during extraction is illustrated in FIG. 5. The amount of toluene (peak area) adsorbed onto the microextractor containing a PDMS fiber (supplied by SUPELCO Co. and having a thickness of 108 μm) is plotted versus the extraction time, which corresponds to the exposure time of the fiber to the water matrix sample. The concentration of toluene was 10 micrograms/liter(μg/l). Initially, the amount of toluene adsorbed by the vibrating fiber increased very rapidly with an increase in extraction time. This trend continued until a steady state was achieved which caused the relationship to level off. The steady state point corresponds to the state of equilibrium between the concentration of the analyte in the stationary phase and in the water matrix sample and defines the extraction time yield and maximum detectivity for the analytical system. According to FIG. 5, the optimum-extraction time for the PDMS-fiber and toluene as an analyte was approximately 4 minutes with fiber vibration compared with over an hour without fiber vibration.

The following example demonstrates the exponential increase in the amount of analyte adsorbed (peak area) between static adsorption on the one hand and fiber vibration and vigorous stirring on the other hand. The sample vial contained LINDANE pesticide in drinking water of a concentration of 10 μl. An automated SPME autosampler was used having an 85 μm polyacrylate fiber. An electric shaver with its shaver head removed to expose the vibrator mechanism was connected by means of a rubber band to a membrane just above the septum of a sample vial. The electric shaver containing an oscillating motor was placed on the door of the autosampler and the shaver was plugged into an AC receptacle for 10 minutes. Table 2 below contains the results.

| Type of Agitation | Surface Integral (Peak Area) | Increase Over Static Method |
|---|---|---|
| None (Static, 10 min.) | 608 | 1 |
| Fiber vibration, 10 min. | 9014 | 14.8 |
| Forceful External Agitation, 10 min. | 11324 | 18.6 |

Without departing from the spirit and scope of this invention, one of ordinary skill in the art can make various changes and modifications to the invention to adapt it to various usages and conditions. As such, these changes and modifications are properly, equitably, and intended to be, within the full range of equivalents of the following claims.

What is claimed is:

1. A device for carrying out solid phase microextraction with analytes contained in a fluid carrier which comprises a fiber, a housing surrounding said fiber, and vibrating means for vibrating said fiber, said housing containing access means so that said carrier and analytes can be brought into contact with the resulting vibrating fiber, wherein said housing is a syringe having a barrel with a first end and a second end and a plunger slidable within said barrel, said plunger having a handle extending from the first end of said barrel, said fiber being mounted within said syringe so that said fiber will move longitudinally within said syringe as said plunger is moved within said barrel, and wherein a hollow needle is connected to said barrel at said second end, said needle containing said fiber, said fiber at least partially extending beyond a free end of said needle when said plunger is depressed within said barrel, said fiber being located within said needle when said plunger is withdrawn relative to said barrel, and wherein said vibrating means is operable to cause said fiber to vibrate when said fiber extends beyond the free end of said needle during microextraction, said vibrating means comprising a vibrator, a membrane for receiving the free end of said needle and an arm operably connected between said vibrator and said membrane.

2. The device of claim 1 wherein said vibrating means also comprises a holder and said membrane is mounted within said holder.

3. The device of claim 1 wherein said syringe is operably connected to an autosampler, said autosampler being programmable to manipulate said plunger and to carry out microextraction and analysis and wherein said vibrator is mounted on said autosampler.

4. The device of claim 3 wherein said autosampler is programmable to activate said vibrator and to cause said membrane, said needle and said fiber to vibrate when said fiber extends beyond the free end of said needle during microextraction.

5. The device of claim 3 wherein said autosampler has means for accommodating at least one container having a septum for receiving the free end of said needle, said container for holding a sample of the analytes contained in the fluid carrier.

6. The device of claim 5 wherein said vibrating fiber extends beyond the free end of said needle and within said container to extract at least one of the analytes contained in the fluid carrier more rapidly using a vibrating fiber than using the non-vibrating fiber during microextraction.

7. The device of claim 5 wherein said vibrating means also comprises aligning means within said vibrator retainer for positioning said membrane in and out of alignment between said needle and said septum.

8. The device of claim 7 wherein said autosampler is programmable to activate said aligning means to move said membrane in alignment between said needle and said septum during microextraction.

9. The device of claim 8 wherein said autosampler is programmable to activate said aligning means to move said membrane out of alignment during analysis.

10. The device of claim 3 wherein said vibrating means also comprises a vibrator retainer for said vibrator, said retainer mounted on said autosampler.

11. The device of claim 1 wherein said fiber is solid and has a coating thereon selected from the group of carbowax, silicone, polyimide, octadecyltrichlorosilane, polymethylvinylchlorosilane, liquid crystalline polyacrylates, grafted self-assembled monolayers and inorganic coatings that is contacted by said carrier and analytes.

12. The device of claim 11 wherein the fiber is selected from the group of polydimethylsiloxane, polyacrylate, graphite, fused silica, and metallic fibers.

13. The device of claim 1 wherein said vibrator comprises a solenoid.

14. Vibrating means for vibrating a fiber of a device for carrying out solid phase microextraction with analytes contained in a fluid carrier which comprises:

a membrane comprising an elastomeric material capable of being pierced by a syringe needle housing a fiber of said device during microextraction;

a solenoid for vibrating said membrane;

a frame;

a retainer mounted on said time for holding said solenoid;

a holder for said membrane; and a retainer arm having one end connected to said retainer and the other end attached to said holder, wherein the fiber housed within the needle is caused to vibrate during microextraction when the needle has pierced said membrane and a septum of a container holding a sample of at least one component contained in a fluid carrier.

15. The vibrating means of claim 14 wherein an electronic circuit operably connected to said solenoid for switching said solenoid among one of three positions consisting of a static ON position, a static OFF position and a static ON, static OFF position.

16. The vibrating means of claim 15 wherein aligning means is operably connected between said solenoid and said retainer for moving said membrane in and out of alignment with said needle and said septum.

17. The vibrating means of claim 16 wherein said electric circuit is programmable to cycle said solenoid between the following positions:

(1) the static ON position which moves said membrane in alignment with said needle and said septum and maintains this position until said syringe needle on said device has pierced said membrane and said septum;

(2) the static ON, static OFF position which attempts to move said membrane in alignment and out of alignment with said needle resulting in the vibration of said membrane, said needle and said fiber while the microextraction takes place;

(3) the static ON position which moves said membrane in alignment with said needle and said septum until said needle has been retracted from said septum and said membrane; and (4) the static OFF position which moves said membrane out of alignment with said needle and said septum.

18. The vibrating means of claim 14 wherein said elastomeric material is rubber.

19. A method of carrying out solid phase microextraction and analysis with analytes contained in a carrier using a vibrating fiber coaxially disposed within a hollow needle, said method comprising placing said vibrating fiber in a container containing said carrier and said analytes and vibrating said fiber relative to said analytes for a sufficient period of time for microextraction to occur, subsequently removing said fiber from said carrier and placing the fiber into a suitable analytical instrument and carrying out desorption with respect to at least one component on said fiber.

20. A method as claimed in claim 19 wherein the vibrating fiber is placed in contact with said carrier for approximately two minutes.

21. A method of carrying out solid phase microextraction and analysis with analytes contained in a carrier using a vibrating fiber contained in a housing, said housing having access means so that said carrier can be brought into contact with said vibrating fiber, said method comprising initiating vibration of said fiber relative to said analytes and contacting said vibrating fiber within said housing for a sufficient time to allow extraction to occur, ending said contact and terminating the vibration thereof and placing the fiber in a suitable analytical instrument in such a manner that desorption occurs with respect to at least one component on said fiber.

22. A method of carrying out solid phase microextraction and analysis with analytes contained in a device having a syringe, a fiber contained therein and vibrating means for vibrating said fiber, said syringe having a barrel and a plunger slidable within said barrel, said plunger having a handle extending from one end of said barrel, with a hollow needle extending from the other end of said barrel, said vibrating means comprising a vibrator, a membrane for receiving a free end of said needle and an arm connected between said vibrator and said membrane, said fiber being mounted within said syringe so that the fiber is located within the needle when the plunger is in a withdrawn position, said fiber extending beyond the free end of said needle when said plunger is in a fully depressed position, said method comprising depressing said plunger to expose said needle, piercing said membrane with said needle, placing said needle in a container containing said carrier and said analytes, vibrating said membrane, fully depressing said plunger for a sufficient time to allow microextraction to occur between the resulting vibrating fiber and said analytes, stopping the membrane from vibrating, moving said plunger to a withdrawn position to cause the fiber to return to an interior of said needle, subsequently placing the needle into an injection port of an analytical instrument, depressing said plunger to expose said fiber so that desorption will occur, subsequently moving said plunger to the withdrawn position and removing said needle from said injection port.

23. A method of analyzing samples containing analytes of interest using a syringe, fiber and vibrating means in combination, said samples being contained in containers having a septum for receiving a needle of the syringe, said fiber being located within said syringe, said syringe having a barrel and a plunger slidable therein, said plunger having a handle extending from one end of said barrel, said vibrating means comprising a vibrator, a membrane for receiving a free end of said needle and an arm connected between said vibrator and said membrane, there being a needle extending from an opposite end of said barrel, said fiber being located within said needle when the plunger is in a withdrawn position and extending beyond said needle when the plunger is in a depressed position, said method utilizing an analytical instrument having an injection port containing a septum for receiving said needle, said method comprising commencing with the plunger in the fiber located within said needle, piercing said membrane and said septum of a container containing a sample to be analyzed with said needle, depressing said plunger to cause said fiber to extend beyond said needle into contact with said sample, vibrating said membrane, contacting the resulting vibrating fiber for a sufficient time to allow microextraction to occur, stopping the membrane from vibrating, moving the plunger to the withdrawn position, removing the syringe from said container, inserting the needle of said syringe through the septum of said injection port of said analytical instrument, depressing the plunger to expose said fiber to said instrument in such a manner that desorption will occur between at least one component on said fiber and said instrument, subsequently moving the plunger to the withdrawn position and withdrawing said needle from said instrument.

24. A method as claimed in claim 23 wherein the extraction and analysis are carried out automatically through the use of an autosampler.

* * * * *